United States Patent [19]

Tanaka et al.

[11] Patent Number: 5,722,942
[45] Date of Patent: Mar. 3, 1998

[54] WOUND COVERING MATERIALS

[75] Inventors: Masaya Tanaka, Kobe; Yasuo Morimoto; Shoichi Harada, both of Osaka; Sadashi Yamashita, Yokosuka, all of Japan

[73] Assignee: Kanebo, Ltd., Tokyo, Japan

[21] Appl. No.: 693,048

[22] PCT Filed: Feb. 13, 1995

[86] PCT No.: PCT/JP95/00198

§ 371 Date: Aug. 16, 1996

§ 102(e) Date: Aug. 16, 1996

[87] PCT Pub. No.: WO95/22354

PCT Pub. Date: Aug. 24, 1995

[30] Foreign Application Priority Data

Feb. 18, 1994 [JP] Japan ................... 6-045013

[51] Int. Cl.[6] ........................................ A61F 5/00
[52] U.S. Cl. ................... 602/56; 602/48; 602/54
[58] Field of Search ................. 602/42-57; 128/888, 128/889-894; 424/443, 445, 446, 447, 448, 449

[56] References Cited

U.S. PATENT DOCUMENTS

| | | | |
|---|---|---|---|
| 4,851,394 | 7/1989 | Kobodera | 514/54 |
| 5,409,703 | 4/1995 | McAnalley et al. | 602/54 X |
| 5,429,591 | 7/1995 | Yamamoto et al. | 602/54 |
| 5,558,861 | 9/1996 | Yamanaka et al. | 424/93.7 |

*Primary Examiner*—Richard J. Apley
*Assistant Examiner*—Kim M. Lee
*Attorney, Agent, or Firm*—Millen, White, Zelano, & Branigan, P.C.

[57] ABSTRACT

A wound covering material comprising 1 part by weight of glucomannan, 0.20–0.99 part by weight of a solubility modifier comprising pullulan or carrageenan, 0.10–12 parts by weight of physiologically acceptable adhesive polymer base, and 0.20–20 parts by weight of at least one plasticizer selected from the group consisting of polyhydric alcohols, sugar alcohols, monosaccharides, disaccharides and oligosaccharides.

8 Claims, No Drawings

WOUND COVERING MATERIALS

In this specification, a "wound" means a scratch, lacerated wound, incised wound, bedsore, and burn.

The present invention relates to wound covering materials suitable for protection and treatment of wounds.

Japanese Patent Publication No. 2-34618 discloses a wound covering material which is formed by kneading glucomannan with or without other naturally occurring polysaccharides in a system comprising at least one compound selected from polyhydric alcohols, sugar alcohols, monosaccharides, disaccharides and oligosaccharides, dissolving the resulting mixture in water, and drying the solution into the form of a film.

This known wound covering material has certain favorable characters such as permeability to water vapor and oxygen, close fit to the wound surface and prevention of excess body fluid from accumulating on the wound surface, and resistance to biodegradation by the body fluid.

However, this wound covering material has low adhesiveness to a normal skin and has a nature to gradually lose its flexibility and elasticity after application to a wound site, thus leading to notable gross shrinking and hardening. Thus, this wound covering material often slides away or detaches from the wound surface, thereby losing its wound sealing and protective function, even when it is fixed onto an immobile part of the body by means of bandages or a surgical tape, let alone when applied to a curved or mobile part such as a joint area. The loss of wound sealing and protective function will lead to drying of the wound surface, resulting in notable retardation of epithelialization compared with wet healing materials used in wound healing in wet environment. Moreover, even if it remains in position over the wound surface, its gross hardening gives rise to the possibility of injury not only to the wound site but also normal tissues surrounding the site. Thus, there is a need to add an improvement to the mentioned known wound covering material.

In the field of food, there are a number of examples of uses of compositions containing glucomannan and pullulan or carrageenan.

For example, Japanese Patent Publication No. 1-59851 discloses food products containing glucomannan and carrageenan and the method for producing them. However, the method for production requires a temperature not lower than 50° C. In contrast, the wound covering material of the present invention may be produced at room temperature. In addition, as the product provided by the above cited production method is intended for eating, it is required to be disintegrated or dissolved within the gastrointestinal tract after taken up, whereas the wound covering material of the present invention will not be dissolved or disintegrated after absorbing exudates from a wound.

Also, Japanese Patent Publication No. 5-49705 discloses a gradually disintegrating, pullulan-containing product which contains a heteromannan. The product, however, is intended for use as a coating membrane for food products and medications, and its major component is pullulan, the amount of the heteromannan contained being not more than the amount by weight of the pullulan contained. Thus, the product differs in the objective and composition from the wound covering material of the present invention which is used by directly applying onto the affected site for protection or healing of the wound.

On the other hand, while the physiologically acceptable adhesive polymer bases employed in the present invention have been utilized as adhesive components in a variety of cataplasms and plasters, it was not known that they confer flexibility and elasticity to the materials when they are incorporated in wound covering materials having glucomannan as the major component.

The objective of the present invention is to provide wound healing materials with prominent sealing and protective function on wound sites which possess adequate adhesiveness, flexibility and elasticity retained even after application onto the wound sites, while maintaining at the same time the favorable characteristics of the wound healing material disclosed in the Japanese Patent Publication No. 2-34618.

As a result of a devoted investigation, the inventors discovered that the above-mentioned objective is met by a wound covering material comprising:

(A) 1 part by weight of glucomannan, (B) 0.20–0.99 part by weight of a solubility modifier comprising pullulan or carrageenan, (C) 0.10–12 parts by weight of a physiologically acceptable adhesive polymer base, and (D) 0.20–20 parts by weight of at least one plasticizer selected from the group consisting of polyhydric alcohols, sugar alcohols, monosaccharides, disaccharides and oligosaccharides, thus completing the present invention.

Glucomannan employed in the present invention is a heteroglycan obtainable from corms of Amorphophallus konjac in which a number of D-glucose and D-mannose molecules are linked through $\beta$-1,4 linkages in a molar ratio of about 2:3.

Pullulan, which may be employed as a solubility modifier in the present invention, is a linear glucan produced by so-called "black yeast" which belongs to deuteromycetes, and those having the molecular weight of about 200,000, which are commercially available, are preferably used.

Carrageenan may also be used as a solubility modifier in the present invention. Carrageenan is a group of polysaccharide sulfuric esters generally obtained from seaweeds, the structure types of which are known, i.e. κ, λ and ι. The carrageenan employed in the present invention comprises at least some amount of κ-type carrageenan.

The following is a description of the amount of the solubility modifier contained, wherein the content is expressed in part by weight unless otherwise specified.

When the amount of the solubility modifier contained is equal to or greater than the 1 part glucomannan, the resulting wound covering material is excessively water soluble and easily disintegrates in contact with the exudates from a wound. On the other hand, when the amount of the solubility modifier contained is less than 0.2 part relative to the 1 part glucomannan, the resulting gel is highly viscous, making it hard to handle, and even when managed to form into a film, it will lack elasticity and adhesiveness required as a wound covering material. These trends are noted regardless of the content of the adhesive polymer base and plasticizer. Thus, in the present invention, the amount of the solubility modifier contained is preferably 0.20–0.99 part, and more preferably 0.50–0.80 part relative to the 1 part glucomannan.

The physiologically acceptable adhesive polymer base employed in the present invention is preferably a rubber adhesive, and more preferably an acrylic adhesive. Among rubber adhesives, those with average molecular weights equal to or lower than 100,000 are preferable, and especially preferable are polybutene (average molecular weight: 500–5,000), polyisobutylene (average molecular weight: 10,000–80,000).

Among acrylic adhesives, acrylic acid alkyl esters are preferably used singly or in the form of a copolymer.

Specific examples include an acrylic acid esters with linear, branched alkyl groups including methyl, ethyl, propyl, butyl, pentyl, hexyl, heptyl, octyl, 2-ethylhexyl, nonyl, isononyl.

Among others, copolymers of methyl acrylate and 2-ethylhexyl acrylate are especially preferable.

When the content of the adhesive polymer base is in excess of 12 parts relative to the 1 part glucomannan, resulting excessive viscosity would render manufacturing difficult and, even if produced, the product would have disadvantages such that it is unpleasant to use because the base is sticky to the skin when applied to a wound or will remain on the skin after the removal of the wound covering material. On the other hand, when the amount of the base contained is less than 0.10 part relative to the 1 part glucomannan, no adequate adhesiveness, flexibility nor elasticity is achievable regardless of the amounts of a solubility modifier and plasticizer. Thus, in the present invention, the amount of the base contained is preferably 0.10–12 parts, and particularly preferably 0.30–6.0 parts relative to the 1 part glucomannan.

The present invention includes at least one plasticizer selected from the group consisting of polyhydric alcohols, sugar alcohols, monosaccharides, disaccharides and oligosaccharides.

Among polyhydric alcohols, propylene glycol, glycerol, ethylene glycol, diethylene glycol, dipropylene glycol and the like are used. Among sugar alcohols, sorbitol, mannitol, maltitol, xylitol and the like are used.

Among monosaccharides, glucose, fructose, galactose and the like are used.

Among disaccharides, saccharose, maltose, lactose and the like are used.

Among oligosaccharides, acid or enzyme decomposed products of starch from sweet potato, potato, Indian corn and the like are used.

The plasticizer in the present invention is preferably a compound selected from glucose, lactose, glycerol and sorbitol or a mixture of two or more of these compounds. Especially preferred are sorbitol, glycerol or their mixture.

When the amount of the plasticizer contained exceeds 20 parts relative to the 1 part the resulting wound covering material becomes excessively water soluble regardless of the amounts of the solubility modifier and adhesive polymer base contained, rendering it readily disintegratable by exudate from the wound. Meanwhile, when the amount of the plasticizer contained is less than 0.20 part relative to the 1 part glucomannan, it is impossible to obtain a wound covering material having adequate flexibility and elasticity. Therefore, the content of the plasticizer in the present invention is 0.20–20 parts, and especially preferably 0.50–15 parts relative to the 1 part of glucomannan.

A preferred embodiment of the present invention is a wound covering material consisting of 1 part of glucomannan, 0.50–0.80 part of pullulan, 0.30–6.0 parts of a copolymer of methyl acrylate and 2-ethylhexyl acrylate, and 0.50–15 parts of glycerol.

The configuration of the wound covering material of the present invention is of a film shape made of the composition consisting of the above components, or that of a two-layered sheet in which the film is placed on a support of, e.g., non-woven fabric of a size greater than that of the film. Such two-layered sheet form of wound covering material may be provided as a better first-aid bandage than those available so far, by, for example, making a first-aid bandage type wound covering material by placing the above film on a part of the surface of a sheet having an adhesive surface.

As a support, a woven geotextile, non-woven fabric or knitting fabric may be used which are composed of natural fibers (cotton, silk, etc.), synthetic fibers (polyethylene, polypropylene, nylon, polyester, polyurethane, etc.) or composite fibers made of them, although no specific limitation applies as long as air permeability is provided. Porous membranes made of natural or synthetic polymers may also be used.

The method of producing the wound covering material of the present invention will be described below.

First, above-identified glucomannan, solubility modifier, adhesive polymer base and plasticizer are added with ethanol and purified water and stirred at room temperature until swelling is achieved to obtain a viscous gel. In this case, 0.5–2.0 parts of ethanol and 30–60 parts of water are generally used relative to 1 part of glucomannan. If the adhesive polymer base is oily and hard to disperse in water, the base may be added after a gel is first made of the other ingredients.

Then, the gel obtained is spread in the thickness of 1–10 mm, preferably 2–8 mm, according to a known method such as a solvent evaporation method or roll coater method, and then subjected to air drying or forced drying to adjust the water content to 1–50%, preferably 5–30%. Thus, a wound covering material in the form of a film having a thickness of 5–1000 μm, preferably 10–500 μm may be obtained.

A two-layered wound covering material may easily be obtained by spreading the gel on a support as illustrated above and drying it, in the same manner as above.

As it has sufficient adhesiveness and flexibility, the wound covering material of the present invention adheres to the normal skin surrounding a wound to thereby seal the wound, and prevents excessive amount of exudates from accumulating on the wound surface and creates an adequate, moist environment at the wound site, thus promoting epithelialization of the wound.

The wound covering material of the present invention is sufficiently flexible and elastic, and its flexibility and elasticity are little affected by changes in environment including temperature and moisture, and it does not undergo biodegradation. Thus, it may be applied for an extended period of time not only to a flat or curved wound surface but also to a wound surface of such a site subjected to bending and stretching as a joint area.

As it is impermeable to high molecular weight substances, the wound covering material of the present invention blocks invasion of pathogenic agents such as bacteria and viruses to the wound surface.

Any of the materials employed in making the wound covering material of the present invention being highly safe, the wound covering material of the present invention is safe and will not induce foreign body responses in the tissue in contact with it.

The present invention will be illustrated further with reference to test examples.

Test Example 1

(Adhesiveness Test)
(1) Test sample (wound covering material)

Wound covering material A: A wound covering material of the present invention cut out of the wound covering material of Example 3 in a size of 2 cm width×12 cm length.

Wound covering material B: A wound covering material of the present invention cut out of the wound covering material of Example 8 in a size of 2 cm width×12 cm length.

Wound covering material X: A wound covering material described in Japanese Patent Publication No. 2-34618, which was prepared by cutting the wound covering material of Comparative Example 1 in a size of 2 cm width×12 cm length.

(2) Test method

The wound covering materials were kept in a room at 20±2° C., 65±2%RH for 30 minutes and then applied to six subjects on the inner side of their forearms cleaned with ethanol for disinfection, immediately followed by passage of a 2-kg roller twice at a rate of 30 cm/min. 10 minutes later, the strength of adhesion was measured by securing the forearm with an applied wound covering material to a vertical stand, peeling off the wound covering material up to 2 cm from the lower end which is then gripped by a metal clip, and measuring the load during continuous peeling off at a rate of 30 cm/min using a Tensilon tensile tester (Trade name: Tensilon RTM-500, produced by Orientech). The significance of adhesive strength of wound covering materials A and B was evaluated against wound covering material X using Fisher's t-test.

In addition, when the test samples were peeled off, the presence, type and extent of side effects (swelling, redness, itching) was evaluated by asking the subjects or visual inspection.

(3) Results

The results are presented in Table 1.

TABLE 1

| Wound covering material | Mean adhesive strength (gf) | | | Side effects |
|---|---|---|---|---|
| | Mean | S.D. | Significance | |
| Wound covering material A | 21.7 | 8.5 | P < 0.05 | no |
| Wound covering material B | 17.7 | 5.2 | P < 0.05 | no |
| Wound covering material X | 7.2 | 3.8 | | no |

As evident from the results, the wound covering materials of the present invention excel over the wound covering material of the comparative example in adhesive strength. Also, no side effect is observable as in the wound covering material of the comparative example.

Test Example 2

(Elasticity Test)

(1) Test sample (wound covering material)

Wound covering material A: A wound covering material of the present invention cut out of the wound covering material of Example 3 in a size of 2.5 cm width×12 cm length.

Wound covering material B: A wound covering material of the present invention cut out of the wound covering material of Example 8 in a size of 2.5 cm width×12 cm length.

wound covering material X: A wound covering material described in Japanese Patent Publication No. 2-34618, which was prepared by cutting the wound covering material of Comparative Example 1 in a size of 2.5 cm width×12 cm length.

(2) Test method

Japanese Industrial Standard L-1018 was applied. The wound covering material was pulled at a rate of 10 cm/min with the length of specimen between grips of 10 cm using Tensilon tensile tester (Trade name: Tensilon RTM-500, produced by Orientech), and the maximum elongation (%) and the maximum load (kgf) at the point were measured. Three tests were performed 3 times for each test sample, elongation per unit load (%/kgf) calculated as an index of elasticity, and the significance of elongation per unit load was evaluated for the wound covering materials A and B against the wound covering material X.

(3) Results

The results are presented in Table 2.

TABLE 2

| Wound covering material | Elongation per unit load (%/kgf) | | |
|---|---|---|---|
| | Mean | S.D. | Significance |
| Wound covering material A | 27.1 | 1.4 | P < 0.05 |
| Wound covering material B | 52.3 | 4.6 | P < 0.01 |
| Wound covering material X | 7.9 | 1.5 | |

As evident from these results, the wound covering materials of the present invention elongate with less load in comparison with the wound covering material of the comparative example and therefore have excellent elasticity.

Test Example 3

(Test in Animal Model-1)

(1) Test sample (wound covering materials)

Wound covering material A: A wound covering material of the present invention cut out of the wound covering material of Example 3 in a size of 4 cm×4 cm.

Wound covering material B: A wound covering material of the present invention cut out of the wound covering material of Example 8 in a size of 4 cm×4 cm.

Wound covering material X: A wound covering material described in Japanese Patent Publication No. 2-34618, which was prepared by cutting the wound covering material of Comparing Example 1 in a size of 4 cm×4 cm.

(2) Test method and evaluation items

The effect on a full thickness skin defect in rat was examined.

Male Wistar rats with body weight of 190-230 g (purchased from Japan SLC), divided into groups of 7 animals each, had, under ether anesthesia, their back shaved using a clipper and an electric shaver and disinfected with alcohol, and then a full thickness skin defect was created by cutting with scissors a circular area of 15 mm in diameter out of the skin on the median line at 4 cm behind the scapulas. A wound covering material was applied to the wound surface and, after placing on it an absorbent cotton piece of 4 mm thick and of the size of 4 cm×4 cm, secured by wrapping an adhesive elastic bandage of 5 cm width×25 cm length (trade name: Benefix, produced by Nippon Sigmax).

Then, the rats were kept one animal/cage with free access to water and food without an exchange of the wound covering materials, and 7 days later the rats were sacrificed by ether inhalation and evaluated for the following items.

1) Adhesiveness to wound surface

Evaluation was made according to the following four stages on the basis of the size of the space between the wound covering material and the wound surface as well as its shift from the wound surface.

Good: The case where the wound covering material shows no shift from its original position, and the wound surface and surrounding skin are closely adhered to by the wound covering material, thereby completely isolated from the outside.

Somewhat good: The case where there is a shift of the wound covering material from its original position, but the wound surface and surrounding skin are closely adhered to by the wound covering material, thereby completely isolated from the outside.

Somewhat poor: The case where the wound covering material is on the wound surface but the wound surface is exposed to the air due to a partial or total detachment of the wound covering material.

Poor: The case where the wound covering material have shifted from its original position, exposing a part or the whole of the wound surface.

2) Change in appearance and deformation

Change in appearance such as distortion, twist, etc. of the wound covering material was visually inspected.

3) Change in flexibility

The flexibility of the wound covering materials removed from the wound surface of the rats was compared with that of unused wound covering materials by bending them by hands, and the changes were evaluated according to the following criteria.

+++: No change in flexibility.

++: A small decrease in flexibility.

+: Flexibility remaining at a practical level.

−: Hardening and total loss of flexibility.

4) Change in length

The length of the wound covering material was measured in the direction of the median line and the rate of shrinkage was determined relative to the length prior to application, then the significance of the rate of shrinkage was determined for the wound covering materials A and B against the rate of shrinkage of the wound covering material x by means of the Dunnett's method.

5) Leak of blood and exudates

The wound covering material, absorbent cotton and adhesive elastic bandage were inspected for the extent of stains with blood or exudates, and evaluated in four stages in accordance with the following criteria.

No leak: No stain in any of the wound contacting surface of the wound covering material, absorbent cotton and adhesive elastic bandage.

Minor leak: A part of the wound contacting surface of the wound covering material is stained with blood or exudates, and no stain is observable in either the absorbent cotton or adhesive elastic bandage.

Medium leak: The whole of the wound contacting surface of the wound covering material is stained with blood or exudates, and no stain is observable in either the absorbent cotton or adhesive elastic bandage.

Major leak: The whole of the wound contacting surface of the wound covering material as well as the absorbent cotton and adhesive elastic bandage are stained with blood or exudates.

6) Hemostatic effect

The traces of bleeding on the wound covering material and the wound surface were visually inspected, and hemostatic effect was determined positive where no trace of bleeding was noted.

(3) Results

1) Adhesiveness to the wound surface

The number of wound covering materials meeting with each criterion is presented in Table 3.

TABLE 3

| Wound covering material | Good | Somewhat good | Somewhat poor | Poor |
|---|---|---|---|---|
| Wound covering material A | 3 | 4 | 0 | 0 |
| Wound covering material B | 1 | 4 | 2 | 0 |
| Wound covering material X | 0 | 0 | 0 | 7 |

As evident from the results, the wound covering materials of the present invention are superior in adhesiveness to the wound surface compared to the wound covering material of the comparative example.

2) Change in appearance and deformation

No significant change in appearance was noted in the wound covering material A and B. In contrast, distortion or twist was observed in the wound covering material X, none of which maintained its original configuration.

Thus, in comparison with the wound covering material of the comparative example, the wound covering material of the present invention exhibits less changes in appearance and deformation.

3) Change in flexibility

The corresponding numbers of wound covering materials are presented in Table 4 according to the aforementioned evaluation criteria.

TABLE 4

| Wound covering material | Evaluation criteria | | | |
|---|---|---|---|---|
| | +++ | ++ | + | − |
| Wound covering material A | 0 | 5 | 2 | 0 |
| Wound covering material B | 0 | 1 | 5 | 1 |
| Wound covering material X | 0 | 0 | 0 | 7 |

As evident from the results, the wound covering material of the present invention exhibits less changes in flexibility in comparison with the wound covering material of the comparative example, therefore being superior in retaining its flexibility.

4) Change in length (Rate of shrinkage)

The results are presented in Table 5.

TABLE 5

| Wound covering material | Shrinkage (cm) | | Rate of shrinkage (%) | | |
|---|---|---|---|---|---|
| | mean | S.D. | mean | S.D. | Significance |
| Wound covering material A | 0.5 | 0.1 | 12.5 | 1.5 | $P < 0.01$ |
| Wound covering material B | 0.7 | 0.1 | 18.2 | 1.4 | $P < 0.01$ |

TABLE 5-continued

| Wound covering | Shrinkage (cm) | | Rate of shrinkage (%) | | |
|---|---|---|---|---|---|
| material | mean | S.D. | mean | S.D. | Significance |
| Wound covering material X | 1.2 | 0.1 | 30.7 | 2.6 | |

As evident from the results, the wound covering material of the present invention exhibits less change in length compared with the wound covering material of the comparative example.

5) Effect on Leak of blood and exudates

The corresponding number of rats meeting with each criterion is presented in Table 6.

TABLE 6

| Wound covering | Evaluation criteria | | | |
|---|---|---|---|---|
| material | No leak | Minor leak | Medium leak | Major leak |
| Wound covering material A | 0 | 1 | 6 | 0 |
| Wound covering material B | 0 | 2 | 5 | 0 |
| Wound covering material X | 0 | 1 | 4 | 2 |

As evident from the results, the wound covering material of the present invention exhibits less leak of blood or exudates from wound surface compared with the wound covering material of the comparative example.

6) Hemostatic effect

Table 7 presents the numbers of the rats in which hemostatic effect was observed, divided by the total number of the rat in each group.

TABLE 7

| Wound covering material | Number of rats in which hemostatic effect was observed/total No. of the rats |
|---|---|
| Wound covering material A | 6/7 |
| Wound covering material B | 5/7 |
| Wound covering material X | 1/7 |

As evident from the results, the wound covering material of the present invention is superior in hemostatic effect compared with the wound covering material of the comparative example.

As noted in 1)–6) above, in comparison with the wound covering material of the comparing example, the wound covering material of the present invention is superior in adhesiveness to a wound surface, and exhibits less change in appearance, flexibility and elasticity when applied to the wound surface. In addition, it exhibit less leaks of blood and exudates, and also superior in hemostatic effect.

Thus, the wound covering material of the present invention is excellent in wound healing accelerating activity.

Test Example 4

(Test in Animal Model-2)

(1) Test Sample (wound covering materials)

Wound covering material A: A wound covering material of the present invention cut out of the wound covering material of Example 3 in a size of 4 cm×4 cm.

Wound covering material C: A wound covering material of the present invention cut out of the wound covering material of Example 4 in a size of 4 cm×4 cm.

Wound covering material X: A wound covering material described in Japanese Patent Publication No. 2-34618, which was prepared by cutting the wound covering material of comparative Example 1 in a size of 4 cm×4 cm.

(2) Test method and evaluation items

The effect on a partial-thickness skin defect in hairless rat was examined.

Female Wistar hairless rats with body weight of 170–200 g (purchased from Japan SLC), divided into groups of 8 animals each, had, under ether anesthesia, their back shaved using an electric shaver and then disinfected with alcohol.

Then, a split thickness skin defect of 1.5 cm×1.5 cm area and 0.5 mm depth was created by peeling the epidermis at 4 cm behind the scapulas by means of a dermatome (trade name: Keisei Baby Freehand Tome D-4010: produced by Keisei Medical Industries). A wound covering material (test sample) was applied to the wound surface and, after placing on it an absorbent cotton piece of 4 mm thick and of the size of 4 cm×4 cm, secured by wrapping an adhesive elastic bandage of 5 cm width×25 cm length (trade name: Benefix, produced by Japan Sigmax). Then, the rats were kept one aminal/cage with free access to water and food without an exchange of the wound covering materials, and 2 days later, the rats were sacrificed by ether inhalation.

Then, tissue specimens were prepared according to a conventional method, and measured for the full length of the wound and the length of regenerated epidermis, under a microscope equipped with an eyepiece provided with a scale, and then the ratio of the length of the regenerated epidermis to the full length of the wound was expressed in percent as the epidermis regeneration rate, and the significance of the epidermis regeneration rate for the wound covering materials A and C are evaluated against the epidermis regeneration rate for the wound covering material X in accordance with the Dunnett's method.

The results are presented in Table 8.

TABLE 8

| Wound covering | Epidermis regeneration rate (%) | | |
|---|---|---|---|
| material | mean | S.D. | Significance |
| Wound covering material A | 85.8 | 8.4 | P < 0.01 |
| Wound covering material C | 96.6 | 2.9 | P < 0.01 |
| Wound covering material X | 44.5 | 12.9 | |

As evident from the results, with the wound covering material of the present invention, wound healing is more rapid than with the wound covering material of the comparative example. Thus, the wound covering material of the present invention is excellent in accelerating wound healing.

Test Example 5

(Skin ulcer treatment test)

The wound covering material of Example 4 cut into the size of 3 cm×4 cm was applied to the skin ulcer (0.5 cm×0.5 cm) with exposed dermis accompanied by minor bleeding, which was created by scratching damage to the skin by a male of 38 years of age with atopic dermatitis on his right calf, and secured with crossing applications of a surgical tape. No pain or itching was noted after the application.

The application was kept for 5 days, during which time he was able to continue a normal life as usual without any problem except for covering the wound covering material with vinyl sheet during bath-taking to prevent water from penetration. 5 days later when it was removed, no accretion was found between the wound covering material and the wound surface, and the wound had been cured with completely regenerated epidermis. As no trace of bleeding was noted, judgement was made that it has a hemostatic effect. The used wound covering material showed no particular change in either appearance or physical properties compared with that before use.

EXAMPLES

The present invention will be described in further detail with reference to examples and a comparative example.

Example 1

2.1 parts by weight of glucomannan (produced by Horiguchi Shoten), 1.4 parts by weight of pullulan (trade name: Pullulan PI-20, produced by Hayashibara Biochemical Research Laboratories), 1 part by weight of emulsion of methyl acrylate and 2-ethylhexyl acrylate copolymer (trade name: Nikasol TS-620, produced by Nippon Carbide Industries, Co., Inc.), 3 parts by weight of glycerol (produced by Wako Pure Chemical Industries, Ltd.), 2 parts by weight of ethanol (produced by Wako Pure Chemical Industries, Ltd.), 90.5 parts by weight of purified water were stirred at room temperature until swelling is achieved, followed by occasional stirring to obtain a viscous gel in one hour. The gel was stirred in a mixer (Titancutter MK-K45, produced by Matsushita Electric Industrial Co., Ltd.) for 2 minutes at room temperature. Then it was heated to 80° C. and filled in an applicator for thin layer plate preparation (produced by Advantech), and spread in a thickness of 4 mm on a glass plate, dried for 4 hours at 60° C. in an electric drying oven (produced by Advantec), giving a film of a thickness of 0.4 mm. This was kept in a fixed temperature/moisture apparatus adjusted to 20±2°C., and 75±5%RH for 4 days to produce a wound covering material.

Examples 2-7

The wound covering material of Examples 2-7 were produced in the same manner as in Example 1 except for variations in the amount of glucomannan, pullulan, emulsion of methyl acrylate and 2-ethylhexyl acrylate copolymer, glycerol, ethanol and purified water. The amounts of glucomannan, pullulan, emulsion of methyl acrylate and 2-ethylhexyl acrylate copolymer, glycerol, ethanol and purified water used in each example are presented in Table 9.

TABLE 9

| Example | Glucomannan | Pullulan | Emulsion of methyl acrylate and 2-ethylhexyl acrylate copolymer | Glycerol | EtOH | Purified water |
| --- | --- | --- | --- | --- | --- | --- |
| Example 2 | 2.1 | 1.4 | 2 | 3 | 2 | 89.5 |
| Example 3 | 2.1 | 1.4 | 5 | 3 | 2 | 86.5 |
| Example 4 | 2.1 | 1.4 | 10 | 3 | 2 | 81.5 |
| Example 5 | 2.69 | 0.81 | 5 | 3 | 2 | 86.5 |
| Example 6 | 2.33 | 1.17 | 5 | 3 | 2 | 86.5 |
| Example 7 | 1.94 | 1.56 | 5 | 3 | 2 | 86.5 |

Example 8

2.1 parts by weight of glucomannan (produced by Horiguchi Shoten), 1.4 parts by weight of pullulan (trade name: Pullulan PI-20, produced by Hayashibara Biochemical Research Laboratories), 3 parts by weight of glycerol (produced by Wako Pure Chemical Industries, Ltd.), 2 parts by weight of ethanol (produced by Wako Pure Chemical Industries, Ltd.), 89.5 parts by weight of purified water were stirred at room temperature until swelling is achieved. Two parts by weight of polybutene (trade name: Polybutene HV-300: produced by Nippon Petrochemicals Co., Ltd.) then was added and stirred to make a uniform mixture, followed by occasional stirring to obtain a viscous gel in one hour. The gel was stirred in a mixer (Titancutter MK-K45, produced by Matsushita Electric Industrial Co., Ltd.) for 2 minutes at room temperature. Then it was heated to 80° C. and filled in an applicator for thin layer plate preparation (produced by Advantec), and spread in a thickness of 4 mm on a glass plate, dried for 4 hours at 60° C. in an electric drying oven (produced by Advantec), giving a film of a thickness of 0.4 mm. This was kept in a fixed temperature/moisture apparatus adjusted to 20±2° C. and 75±5%RH for 4 days to produce a wound covering material.

Examples 9-12

The wound covering material of Examples 9-12 were produced in the same manner as in Example 8 except for variations in the amount of glucomannan, pullulan, polybutene, ethanol and purified water. The amounts of glucomannan, pullulan, polybutene, glycerol, ethanol and purified water used in each example are presented in Table 10.

TABLE 10

| Example | Glucomannan | Pullulan | Polybutene | Glycerol | EtOH | Purified Water |
| --- | --- | --- | --- | --- | --- | --- |
| Example 9 | 2.1 | 1.4 | 5 | 3 | 2 | 86.5 |
| Example 10 | 2.69 | 0.81 | 2 | 3 | 2 | 89.5 |
| Example 11 | 2.33 | 1.17 | 2 | 3 | 2 | 89.5 |
| Example 12 | 1.94 | 1.56 | 2 | 3 | 2 | 89.5 |

Example 13

2.1 parts by weight of glucomannan (produced by Horiguchi Shoten), 1.4 parts by weight of pullulan (trade name: Pullulan PI-20, produced by Hayashibara Biochemical Research Laboratories), 3 parts by weight of glycerol (produced by Wako Pure Chemical Industries, Ltd.), 2 parts by weight of ethanol (produced by Wako Pure Chemical Industries, Ltd.), 89.0 parts by weight of purified water were stirred at room temperature until swelling is achieved.

Then, 2.5 Parts by weight of polyisobutylene (trade name: Himol 4H: produced by Nippon Petrochemicals) was added and stirred to make a uniform mixture, followed by occasional stirring to obtain a viscous gel in one hour. The gel was stirred in a mixer (trade name: Titancutter MK-K45, produced by Matsushita Electric Industrial Co., Ltd.) for 2 minutes at room temperature. Then it was heated to 80° C. and filled in an applicator for thin layer plate preparation (produced by Advantec), and spread in a thickness of 4 mm on a glass plate, dried for 4 hours at 60° C. in an electric drying oven (produced by Advantec), giving a film of a thickness of 0.4 mm. This was kept in a fixed temperature/moisture apparatus adjusted to 20±2° C., and 75±5%RH for 4 days to produce a wound covering material.

Examples 14–16

The wound covering material of Examples 14–16 were produced in the same manner as in Example 13 except for variations in the amount of glucomannan, pullulan, polyisobutylene, ethanol and purified water. The amounts of glucomannan, pullulan, polyisobutylene, glycerol, ethanol and purified water used in each example are presented in Table 11.

TABLE 11

| Example | Gluco-mannan | Pullulan | Polyiso-butylene | Glycerol | EtOH | Purified Water |
|---|---|---|---|---|---|---|
| Example 14 | 2.69 | 0.81 | 2.5 | 3 | 2 | 89.0 |
| Example 15 | 2.33 | 1.17 | 2.5 | 3 | 2 | 89.0 |
| Example 16 | 1.94 | 1.56 | 2.5 | 3 | 2 | 89.0 |

Example 17

2.1 parts by weight of glucomannan (produced by Horiguchi Shoten), 1.4 parts by weight of pullulan (trade name: Pullulan PI-20, produced by Hayashibara Biochemical Research Laboratories), 3 parts by weight of glycerol (produced by Wako Pure Chemical Industries, Ltd.), 2 parts by weight of ethanol (produced by Wako Pure Chemical Industries, Ltd.), 89.5 parts by weight of purified water were stirred at room temperature until swelling is achieved. Then, 1 part by weight of polybutene (trade name: Polybutene HV-300, produced by Nippon Petrochemicals Co., Ltd.), 1 part by weight of polyisobutylene (trade name: Himol 4H: produced by Nippon Petrochemicals Co., Ltd.) then were added and stirred to make a uniform mixture, followed by occasional stirring to obtain a viscous gel in one hour. The gel was stirred in a mixer (trade name: Titancutter MK-K45, produced by Matsushita Electric Industrial Co., Ltd.) for 2 minutes at room temperature. Then it was heated to 80° C. and filled in an applicator for thin layer plate preparation (produced by Advantec), and spread in a thickness of 4 mm on a glass plate, dried for 4 hours at 60° C. in a hot air blower dryer (produced by Advantec), giving a film of a thickness of 0.4 mm. This was kept in a fixed temperature/moisture apparatus adjusted to 20±2° C. and 75±5%RH for 4 days to produce a wound covering material.

Examples 18–34

The same procedure was followed as in Examples 1–17 except that the gel, instead of direct spreading on a glass plate, was spread on a polyester cotton non-woven fabric of 1 mm thick (trade name: Espandy, produced by Kanebo, Ltd.) secured on a glass plate using an adhesive tape, to produce a 2-layered sheet having a wound surface contacting layer of 0.4 mm thick. This then was kept in a fixed temperature/moisture apparatus adjusted to 20±2° C. and 75±5%RH for 4 days to produce wound covering materials of Examples 18–34. The gel used in each Example is shown in Table 12.

TABLE 12

| Example | Configuration |
|---|---|
| Example 18 | The gel of Example 1 was spread on polyester cotton non-woven fabric |
| Example 19 | The gel of Example 2 was spread on polyester cotton non-woven fabric |
| Example 20 | The gel of Example 3 was spread on polyester cotton non-woven fabric |
| Example 21 | The gel of Example 4 was spread on polyester cotton non-woven fabric |
| Example 22 | The gel of Example 5 was spread on polyester cotton non-woven fabric |
| Example 23 | The gel of Example 6 was spread on polyester cotton non-woven fabric |
| Example 24 | The gel of Example 7 was spread on polyester cotton non-woven fabric |
| Example 25 | The gel of Example 8 was spread on polyester cotton non-woven fabric |
| Example 26 | The gel of Example 9 was spread on polyester cotton non-woven fabric |
| Example 27 | The gel of Example 10 was spread on polyester cotton non-woven fabric |
| Example 28 | The gel of Example 11 was spread on polyester cotton non-woven fabric |
| Example 29 | The gel of Example 12 was spread on polyester cotton non-woven fabric |
| Example 30 | The gel of Example 13 was spread on polyester cotton non-woven fabric |
| Example 31 | The gel of Example 14 was spread on polyester cotton non-woven fabric |
| Example 32 | The gel of Example 15 was spread on polyester cotton non-woven fabric |
| Example 33 | The gel of Example 16 was spread on polyester cotton non-woven fabric |
| Example 34 | The gel of Example 17 was spread on polyester cotton non-woven fabric |

Comparing Example 1

2.1 parts by weight of glucomannan (produced by Horiguchi Shoten), 1.4 parts by weight of pullulan (trade name: Pullulan PI-20, produced by Hayashibara Biochemical Research Laboratories), 3 parts by weight of glycerol (produced by Wako Pure Chemical Industries, Ltd.), 2 parts by weight of ethanol (produced by Wako Pure Chemical Industries, Ltd.), 91.5 parts by weight of purified water were stirred at room temperature until swelling is achieved, followed by occasional stirring to obtain a viscous gel in 1 hour. The gel was stirred in a mixer (trade name: Titancutter MK-K45, produced by Matsushita Electric Industrial Co., Ltd.) for 2 minutes at room temperature. Then it was heated to 80° C. and filled in an applicator for thin layer plate preparation (produced by Advantech), and spread in a thickness of 5 mm on a glass plate, dried for 4 hours at 60° C. in an electric drying oven (produced by Advantec), giving a film of a thickness of 0.4 mm. This was kept in a fixed temperature/moisture apparatus adjusted to 20±2° C., and 75±5%RH for 4 days to produce a wound covering material.

We claim:

1. A wound covering material comprising an adhesive film consisting essentially of:

(A) 1 part by weight of glucommman, (B) 0.20–0.99 parts by weight of a solubility modifier selected from the group consisting of pullulan and carrageenan, (C) 0.10–12 parts by weight of a physiologically acceptable alkyl acrylate adhesive polymer base, (D) 0.20–20 parts by weight of a plasticizer selected from the group consisting of polyhydric alcohols, sugar alcohols, monosaccharides, disaccharides and oligosaccharides.
and 1–50% by weight of the film of water.

2. The wound covering material of claim 1 which is produced by forming a dispersion of said components (A) through (D) in a mixture of 0.5–2.0 parts of ethanol and 30–60 parts of water per 1 part of glucomannan, applying the dispersion onto an air permeable backing to form a film having a thickness of 1–10 mm, and then drying the film to reduce the water content thereof to 1–50%.

3. The wound covering material of claim 1, wherein the plasticizer is selected from the group consisting of glycerol, sorbitol and a mixture thereof.

4. The wound covering material of claim 1, wherein the solubility modifier is pullulan, the alkyl acrylate adhesive polymer base is a copolymer of methyl acrylate and 2-ethylhexyl acrylate and the plasticizer is glycerol.

5. The wound covering material of claim 1, further comprising a support to which the adhesive film is adhered.

6. The wound covering material of claim 1, wherein the support is a fabric or a porous polymer membrane.

7. A wound covering material comprising an adhesive film consisting essentially of:

(A) 1 part by weight of glucomannan, (B) 0.50–0.80 parts by weight of pullulan, (C) 0.30–6.0 parts by weight of a methyl acrylate\2-ethyl hexyl acrylate copolymer, (D) 0.50–15 parts by weight of glycerol, and (E) 1–50% by weight of the film of water.

8. The wound covering material of claim 7 which is produced by forming a dispersion of said components (A) through (D) in a mixture of 0.5 to 2.0 parts of ethanol and 30–60 parts of water per 1 part of glucomannan, applying the dispersion onto an air permeable backing to form a film having a thickness of 1–10 mm, and then drying the film to reduce the water content thereof to 1–50%.

* * * * *

UNITED STATES PATENT AND TRADEMARK OFFICE
CERTIFICATE OF CORRECTION

PATENT NO. : 5,722,942
DATED : March 3, 1998
INVENTOR(S) : Masaya TANAKA et al.

It is certified that error appears in the above-identified patent and that said Letters Patent is hereby corrected as shown below:

On the title page, item [73]

IN THE ASSIGNEE SECTION:

Please add --UNICOLLOID, INC. of KANAGAWA-KAN, JAPAN-- as the second assignee of the application.

Signed and Sealed this

Twentieth Day of October, 1998

Attest:

BRUCE LEHMAN

Attesting Officer    Commissioner of Patents and Trademarks